United States Patent [19]

Caporiccio

[11] Patent Number: 5,041,588

[45] Date of Patent: Aug. 20, 1991

[54] CHEMICALLY REACTIVE FLUORINATED ORGANOSILICON COMPOUNDS AND THEIR POLYMERS

[75] Inventor: Gerardo Caporiccio, Midland, Mich.

[73] Assignee: Dow Corning Corporation, Midland, Mich.

[21] Appl. No.: 374,847

[22] Filed: Jul. 3, 1989

[51] Int. Cl.$^5$ ............................................. C07F 7/04
[52] U.S. Cl. ................................... 556/413; 556/430; 556/440; 556/442; 556/463; 556/485; 556/488
[58] Field of Search ............... 556/488, 463, 485, 442, 556/440, 413, 430

[56] References Cited

U.S. PATENT DOCUMENTS

| | | | |
|---|---|---|---|
| 2,651,651 | 9/1953 | Simons et al. | 556/488 |
| 2,686,194 | 8/1954 | Passino et al. | 556/488 |
| 2,800,494 | 7/1957 | Haluska | 556/488 |
| 3,188,336 | 6/1965 | Haszeldine | 556/448 |
| 3,579,557 | 5/1971 | Brooks et al. | 556/488 |
| 4,731,170 | 3/1988 | Caporiccio . | |

FOREIGN PATENT DOCUMENTS

| | | | |
|---|---|---|---|
| 552504 | 2/1958 | Canada | 556/488 |
| 0200908 | 11/1986 | European Pat. Off. . | |
| 2511187 | 9/1975 | Fed. Rep. of Germany | 556/488 |
| 895592 | 5/1962 | United Kingdom | 556/488 |
| 1075101 | 7/1967 | United Kingdom | 556/488 |

Primary Examiner—Joseph L. Schofer
Assistant Examiner—N. Sarofim
Attorney, Agent, or Firm—Robert Spector

[57] ABSTRACT

Chemically reactive fluorinated organosilicon compounds as described for use as, e.g., lubricants, sealants and elastomers, are described corresponding to the formulae $$X_2R^1{}_2Si \qquad \text{I}$$

or $$XR^2{}_2Si(R^3SiR^2{}_2)_zX \qquad \text{II}$$

where X a represents a reactive group selected from a halogen, hydroxyl, alkoxy, acetoxy, amino, alkyl amino or dialkyl amino, z is from 1 to 5, inclusive, at least one of the $R^1$ radicals and at least one of the $R^2$ radicals bonded to each of the silicon atoms are derived from: 1) a monovalent telomer of fluorinated olefins; 2) a monovalent cotelomer of (a) chlorotrifluoroethylene and a fluoropropene, (b) chlorotrifluoroethylene and vinylidene fluoride, (c) chlorotrifluoroethylene, a fluoropropene and a fluoroethylene, fluoride and a fluoropropene, (d) vinylidene, (e) a fluoroethylene and a perfluoroalkyl vinyl ether, (f) a fluoroethylene, chlorotrifluoroethylene and a perfluoroalkyl vinyl ether, (g) a fluoroethylene, a fluoropropene and vinylidene fluoride, (h) a fluoroethylene, chlorotrifluoroethylene and vinylidene fluoride, or (i) a fluoropropene, chlorotrifluoroethylene and vinylidene fluoride, wherein the telomers and cotelomers are bonded to silicon through a non-halogenated alkylene radical of 2,3,4 carbon atoms and the alkyl groups of the perfluoroalkyl vinyl ethers have from 1 to 3 carbon atoms; or 3) a monovalent oligomer of fluorinated oxetanes and oxiranes, where said oligomer is bonded to silicon by a non-halogenated ethylene or trimethylene radical; any remaining $R^1$ and $R^2$ radicals are an alkyl of 1 to 4 carbon atoms, alkenyl, perfluoroalkyl-di-methylene, trimethylene or tetramethylene, phenyl or a perfluoroalkyl-substituted phenyl radicals, wherein the perfluoroalkyl portion of the perfluoroalkyl-substituted radicals has 1 to 4 carbon atoms; and $R^3$ is derived from a divalent telomer or cotelomer from the same group of olefins and perfluoroalkyl vinyl ethers, a divalent oligomer derived from fluorinated oxetanes and fluorinated oxiranes, or is $-[CH_2CH_2CH_2OC(CF_3)_2]_2Ph$, wherein PH represents a meta-phenylene radical.

10 Claims, No Drawings

CHEMICALLY REACTIVE FLUORINATED ORGANOSILICON COMPOUNDS AND THEIR POLYMERS

BACKGROUND OF THE INVENTION

This invention relates to novel organosilicon compounds. More particularly, this invention relates to chemically reactive fluorinated organosilicon compounds, wherein the majority of the organic groups bonded to silicon are telomer or cotelomer derivatives of a specified group of fluoroolefins, or derivatives from oligomers of a fluorinated oxetane or a fluorinated oxirane, and to the polymers thereof. The polymers prepared by polycondensation of these organosilicon compounds are characterized by chemical resistance, low coefficient of friction, excellent electrical insulating properties and a high resistance to organic solvents and degradation. Depending on the structure of the constituents, their distribution, the molecular weight of the polymers and presence of units carrying crosslinking situs along the chain, the final compounds can be used as, e.g., fluids, elastomers, sealants, barrier and release materials, coatings and resins.

The proper use of fluorine substitution on organic polymers to improve both the thermal and chemical resistance of the polymer, in addition to providing antiwear, optical and electrical insulating properties to the polymers, is well known.

The most common and commercially available fluorosilicones are typically represented by structures containing the 3,3,3-trifluoropropyl radical bonded to silicon. Many copolymers containing this radical, and longer fluoroalkyl radicals, or containing short alpha, omega-fluoroalkylene radicals linking two silicon atoms along the chain, are disclosed in the journal and patent literature. See, e.g., U.S. Pat. No. 3,647,740. All of these products suffer to a greater or lesser extent from the tendency to depolymerize under thermal, catalytic or hydrolytic conditions, and their resistance to some organic solvents may be only slightly improved relative to non-fluorinated silicone materials. See, e.g., Ind. Eng. Chem. Prod. Res. Dev., Vol. 23, page 600, (1984). These shortcomings depend on the high frequency along the chain of polar siloxy (SiO) groups and on the relatively low fluorine content of known fluorosilicones.

An objective of this invention is to provide a novel class of reactive organosilicon compounds that can be converted to polymers, fluids, elastomers and resins which do not exhibit the aforementioned disadvantages of prior art fluorosilicone materials.

SUMMARY OF THE INVENTION

The objective of this invention is achieved by providing 1) novel reactive fluorinated organosilicon compounds, wherein the majority of the organic groups bonded to silicon are derived from a specified class of telomers and/or cotelomers of fluoroolefins, and for from oligomers of fluorooxiranes or of fluorooxetanes, and 2) methods for preparing these novel compounds and the polymers thereof.

This invention provides reactive fluorinated organosilicon compounds corresponding to the formulae:

$$X_2R^1_2Si \quad \quad I$$

or $$XR^2_2Si(R^3SiR^2_2)_zX \quad \quad II$$

where X represents a reactive group selected from the group consisting of halogen, preferably bromine or chlorine, hydroxyl, alkoxy, acetoxy, amino, alkyl amino and dialkyl amino, z is from 1 to 5, inclusive, at least one of the $R^1$ radicals of formula I and at least one of the $R^2$ radicals bonded to each of the silicon atoms of formula II are derived from the group consisting of:

1) monovalent telomers of fluorinated olefins selected from the group consisting of chlorotrifluoroethylene, vinylidene fluoride and trifluoroethylene;

2) monovalent cotelomers of (a) chlorotrifluoro-ethylene and a fluoropropene selected from the group consisting of hexafluoropropene, 1-H-pentafluoropropene and 2-H-pentafluoropropene, (b) chlorotrifluoroethylene and vinylidene fluoride, (c) chlorotrifluoroethylene, said fluoropropenes and a fluoroethylene selected from the group consisting of tetrafluoroethylene and trifluoroethylene, (d) vinylidene fluoride and said fluoropropenes, (e) said fluoropropenes and a perfluoroalkylvinyl ether, (f) said fluoroethylenes, chlorotrifluoroethylene and a perfluoroalkyl vinyl ether, (g) said fluoroethylenes, said fluoropropenes and vinylidene fluoride, (h) said fluoroethylenes, chlorotrifluoroethylene and vinylidene fluoride, or (i) said fluoropropenes, chlorotrifluoroethylene and vinylidene fluoride, wherein the telomers and cotelomers are bonded to silicon through a non-halogenated alkylene radical with 2, 3, 4 carbon atoms and the alkyl groups of said perfluoroalkyl vinyl ethers contain from 1 to 3 carbon atoms; and 3) monovalent oligomers of fluorinated oxetanes and oxiranes, wherein said oligomers are bonded to silicon through a group containing a non-halogenated ethylene or a non-halogenated trimethylene radical; any remaining $R^1$ and $R^2$ radicals are selected from the group consisting of an alkyl with 1 to 4 carbon atoms, alkenyl, perfluoroalky-dimethylene, -trimethylene or -tetramethylene, phenyl or perfluoroalkyl-substituted phenyl radicals, wherein the perfluoroalkyl portion of said perfluoroalkyl-substituted radicals contains from 1 to 4 carbon atoms; and $R^3$ is derived from a divalent telomer or cotelomer of the same group of olefins and perfluoroalkyl vinyl ethers, a divalent oligomer derived from fluorinated oxetanes and fluorinated oxiranes, or is —[CH$_2$CH$_2$CH$_2$OC(CF$_3$)$_2$]$_2$Ph, wherein Ph represents a meta-phenylene radical.

Preferred telomers and cotelomers represented by $R^1$ and $R^2$ correspond to the following formulae:

Rf(C$_2$F$_4$)$_t$(C$_2$H$_2$F$_2$)$_u$—(C$_2$ClF$_3$)$_q$—C$_1$H$_{21}$—,
Rf(C$_2$H$_2$F$_2$)$_p$(C$_2$ClF$_3$)$_q$—C$_1$H$_{21}$—,
Rf(C$_2$H$_2$F$_2$)$_t$(C$_2$F$_4$)$_u$(C$_3$F$_6$)$_q$—C$_1$H$_{21}$,
Rf(C$_2$H$_2$F$_2$)$_t$(C$_2$ClF$_3$)$_u$(C$_3$F$_6$)$_q$—C$_1$H$_{21}$—,
Rf(C$_2$ClF$_3$)$_n$—CF$_2$CF(R$^4$)—C$_1$H$_{21}$—,
Rf(C$_2$ClF$_3$)$_p$—(C$_3$F$_6$)$_q$—C$_3$F$_6$—C$_1$H$_{21}$—,
Rf(C$_2$F$_4$)$_t$(C$_2$ClF$_3$)$_u$—(C$_3$F$_6$)$_q$—CF$_2$CF(R$^4$)—C$_1$H$_{21}$—,
Rf(C$_2$F$_4$)$_t$(C$_2$ClF$_3$)$_u$—[C$_2$F$_3$(ORf)]$_q$C$_2$F$_4$C$_1$H$_{21}$—
Rf(C$_2$H$_2$F$_2$)$_p$(C$_3$F$_6$)$_q$—C$_1$H$_{21}$—, or
Rf(C$_2$F$_4$)$_p$[C$_2$F$_3$(ORf)]$_q$—C$_1$H$_{21}$— where the repeating units of said cotelomers are randomly distributed along the chain.

The oligomers represented by $R^1$ and $R^2$ correspond to the formulae:

R'fO(C$_3$F$_6$O)$_m$CF(CF$_3$)CA$_2$OC$_3$H$_6$—,
C$_3$F$_7$O(C$_3$H$_2$F$_4$O)$_m$—CH$_2$CF$_2$CA$_2$OC$_3$H$_6$—, or
R$^5$O(CF$_3$C$_2$H$_3$O)$_m$C$_3$H$_6$—.

In the foregoing formulae "A" represents hydrogen or fluorine, $R^4$ represents fluorine or a trifluoromethyl group, $R^5$ represents an alkyl or fluoroalkyl radical, Rf is —$CF_3$, —$C_2F_5$, —$C_3F_7$ or —$C_4$, $F_9$ and R'f is —$CF_3$, $C_2F_5$ or $C_3F_7$; any $R^1$ and $R^2$ radicals that do not represent a telomer, cotelomer or oligomer as defined hereinabove preferably represents methyl,3,3,3-trifluoropropyl, phenyl or a perfluoroalkyl substituted phenyl, where said perfluoroalkyl group contains from 1 to 3 carbon atoms, and the value of "1" is 2, 3, or 4.

$R^3$ is preferably selected from the group consisting of
—$C_1H_{21}$—$C_3F_6(C_2ClF_3)_n(T)C_3F_6$—$C_1H_{21}$—
—$C_1H_{21}$—$C_2F_4(C_2ClF_3)_u(T)$ $(C_2F_4)_t(C_2F_3ORf)_q$—$C_2F_4$—$C_1H_{21}$—
—$C_1H_{21}$—$C_3F_6(C_2ClF_3)_u(T)$ $(C_2F_4)_t(C_3F_6)_q$—$C_3F_6$—$C_1H_{21}$—,.
—$C_1H_{21}C_3F_6(C_2ClF_3)_p(T)$ $(C_3F_6)_q$—$C_3F_6C_1H_{21}$—,
—$C_1H_{21}(C_2H_2F_2)_p(T)$ $(C_3F_6)_q$—$C_1H_{21}$—,
—$C_1H_{21}(C_2F_4)_p(T)$ $(C_2F_3ORf)_qC_1H_{21}$—,
—$C_1H_{21}(C_2H_2F_2)_p(T)$ $(C_2ClF_3)_q$—$C_1H_{21}$—,
—$C_1H_{21}(C_2H_2F_2)_t(C_2F_4)_u(T)$ $(C_3F_6)_q$—$C_1H_{21}$—,
—$C_3H_6O(CF_3)_2C$—$C_6H_4$—$C(CF_3)_2OC_3H_6$—,
—$C_3H_6OCA_2CF_2CH_2O(C_3H_2F_4O)_gT'O(C_3H_2F_4O)_g$—$CH_2CF_2CA_2OC_3H_6$—,
—$C_3H_6OCH_2CF_2O(C_2F_4O)_h(CF_2O)_iCF_2CH_2OC_3H_6$—, or
—$C_3H_6OCA_2$—$CF(CF_3)O(C_3F_6O)_gT'O(C_3F_6O)_gCF(CF_3)CA_2OC_3H_6$—.

T is selected from the group consisting of —$C_2F_4$—, —$C_3F_6$—, —$C_2ClF_3$—, —$C_6F_xH_{(4-x)}$—and $O[C_6F_xH_{(4-x)}]_2$, where x is from 2 to 4, inclusive;

T'is selected from the group consisting of —$C_2F_4$—, —$C_4F_8$—, —$C_5F_{10}$—and —$(C_2F_4)_2O$—;

the repeating units are randomly distributed along the chain;

the value of "1" is 2, 3, 4;

the value of n is from 1 to 20, inclusive, preferably from 1 to 10;

the value of p/q is from 2 to 10, inclusive and the value of p+q is from 2 to 20, preferably from 2 to 10;

the value of t+u/q is from 2 to 10, inclusive, the value of t/u is from 0.1 to 10, and the value of t+u+q is from 2 to 20, inclusive, preferably lower than 10;

the value of m is from 1 to 20, inclusive, preferably from 1 to 10;

g is from 1 to 20, inclusive, preferably from 2 to 10; and h/i is from 0.5 to 20, inclusive and h+i is from 8 to 100, inclusive, preferably from 8 to 20.

The repeating units of the present fluorinated organosilicon compounds are randomly distributed within the molecules and the silicon atoms of these compounds are bonded by a non-halogenated alkylene radical containing 2, 3, or 4 carbon atoms to telomers or cotelomers of the fluoroorganic compounds, or by a bivalent group containing a non-halogenated dimethylene or non-halogenated trimethylene radical to oligomers of the fluorinated oxetanes and oxiranes defined hereinbefore. One of the $R^1$ radicals present in formula I and one of the terminal $R^2$ radicals located on each of the silicon atoms in formula II can represent alkyl, alkenyl, aryl, perfluoroalkyl-substituted phenyl and/or monovalent fluorinated alkyl radicals corresponding to the formula —$C'_1H_{21}R^6$, where "1" is 2, 3, 4, and $R^6$ is a perfluoroalkyl radical containing from 1 to 4 carbon atoms. $R^3$ can be a divalent telomer, cotelomer or oligomer as defined hereinbefore or it can be —$[(CH_2)_3OC(CF_3)_3]_2$Ph, where Ph represents m-phenylene.

DETAILED DESCRIPTION OF THE PREFERRED EMBODIMENTS

Polyorganosiloxanes prepared using the present organosilicon compounds as at least a portion of the organosilicon reactants exhibit a high thermochemical resistance, low values of surface energy, and a low refractive index.

The physical properties for the materials described herein as fluoro hybrid polysiloxanes depend on the structural ratio:

$$\frac{(SiO) + (C - O)}{(C - C) + (Si - C)}$$

formed by the bonds present along the chain. Particularly, the amount of the sum of the bonds (Si—0)+(C—0) controls the chain flexibility and the related properties (glass transition temperature, anti-impact). The sum of the bonds (C-C) +(Si-C) controls the rigidity and the mechanical, thermal, and reversion resistance. Moreover, the contents of fluorine controls the thermoresistance and the hydro-lipo-phobic character of the materials besides other properties typical of fluorocarbon materials (optical, electrical, anti-wear).

The presence of silicon allows some geometrical arrangements of the surrounding groups, due to the large radius of the atom, and especially allows easy crosslinking reactions. Depending upon their structure, molecular weight, and the presence or not of intermolecular crosslinking, these polyorganosiloxanes are useful as fluids, rubbers exhibiting a high solvent and thermal resistance, barrier and release coatings and as resins exhibiting excellent optical and electrical insulating properties. Preparation of these polyorganosiloxanes is discussed below.

The Fluoroolefins and Telomers Thereof

One class of the radicals bonded to the silicon according to the invention is prepared from fluorinated telomers and cotelomers that are, in turn, prepared from fluoroolefins containing two or three carbon atoms. In some instances a perfluoroalkyl vinyl ether can be used as a comonomer. The fluoroolefins can contain at most one chlorine or at most two hydrogen atoms per molecule, with the proviso that chlorine and hydrogen are not present in the same molecule. The remaining substituents on the carbon atoms of the fluoroolefins are fluorine atoms.

If a very high thermal stability is desired, when chlorotrifluoroethylene is used to synthesize the telomers or cotelomers respectively with non-hydrogenated vinyl compounds, care must be taken during formation of the telomer or cotelomer and the end capping step to avoid the presence of a chlorine atom on each of two adjacent carbon atoms that form the sequence =CCl—CCl= or the presence of the sequence =HC—CCl=. This precaution will avoid dehalogenation or dehydrohalogenation at high temperatures in the presence of metals and-/or oxygen and/or catalysts, which decreases the stability of the final organosilicon compound during use.

The perfluoroalkyl group present on the perfluoroalkylvinyl ethers that can be cotelomerized with chlorotrifluoroethylene or tetrafluoroethylene in accordance with the present invention can be perfluoromethyl, -ethyl, or -propyl.

The fluorinated olefins and ethers, referred to hereinafter as fluorovinyl compounds, used to prepare the present telomers and cotelomers are selected from the classes described in detail in this specification and polymerized in the proper sequence if the final organosilicon compound is to exhibit the high levels of chemical inertness and other properties required for critical conditions of use at high temperature, and aggressive environments. The presence of fluoropolyoxaalkylene groups such as the oligomers of fluorooxiranes and fluorooxetanes improve rheological properties at low temperatures and the viscosity index of the present compounds in the fluid form.

A fluoroalkyl-substituted benzene, a perfluoroalkyl-substituted dimethylene, or -trimethylene radical, a phenyl radical, or an alkenyl radical can be used in place of a portion of the telomers represented by $R^1$ or terminal $R^2$ radicals in the general formulae of the present organosilicon compounds, and for a portion of the reactive silanes that are then polycondensated to final fluorinated silicones.

A preferred method for preparing the telomers or cotelomers is by a radical-initiated telomerization of fluorinated vinyl compounds selected from the groups defined hereinbefore. These fluorovinyl compounds are chlorotrifluoroethylene (referred to sometimes hereinafter as CTFE), vinylidene fluoride, hexafluoropropene, 1-H-pentafluoro-propene, 2-H-pentafluoropropene, tetrafluoroethylene, trifluoroethylene, perfluoromethyl vinyl ether, perfluoroethyl vinyl ether, and perfluoropropyl vinyl ether. Chlorotrifluoroethylene, vinylidene fluoride and trifluoroethylene can be telomerized individually. Binary or ternary systems of vinyl compounds that can be cotelomerized include (a) chlorotrifluoroethylene and a fluoropropene, selected from the group consisting of hexafluoropropene, 1-H-pentafluoropropene and 2-H-pentafluoropropene, (b) chlorotrifluoroethylene and vinylidene fluoride, (c) chlorotrifluoroethylene, said fluoropropenes and a fluoroethylene selected from the group consisting of tetrafluoroethylene and trifluoroethylene, (d) vinylidene fluoride and said fluoropropenes, (e) said fluoroethylene and a perfluoroalkyl vinyl ether, (f) said fluoroethylenes, chlorotrifluoroethylene and a perfluoroalkylvinyl ether, (g) said fluoroethylenes, said fluoropropenes and vinylidene flouride, or (i) said fluoropropenes, chlorotrifluoroethylene and vinylidene fluoride.

The telomerization and cotelomerization of the fluorovinyl compounds can be initiated by bromo- or iodo-substituted telogens represented by the formula RfX or XR′fX, where Rf and R′f are as previously defined in this specification and X is bromine or iodine. These telogens belong to a group that includes, but is not limited to, $CF_3I$, $C_2F_5I$, n- or iso-$C_3F_7I$, n-$C_4F_9I$, $C_2F_5Br$, $CF_3CFBRCF_2Br$, $CF_3CFICF_2I$, $CF_2Br$ $CFClBr$, $CF_2ICF_2I$, $I(C_2F_4)_nI$ (n=2-10); $C_2F_3ClBrI$ and $C_3F_6BrI$ derived from addition of BrI to the fluoroolefins $C_2F_3Cl$ and $C_3F_6$; $C_6F_xH_{4-x}I_2$ (diiodofluoro benzene), and $O(C_6F_xH_{4-x}I)_2$ (diiodofluoro diphenyl ether), where x is from 2 to 4.

The telomers and cotelomers prepared from the foregoing monoiodo or monobromo telogens are linked through non-halogenated alkylene radicals of 2, 3, 4 carbon atoms to a silicon atom using methods described in the following paragraphs to prepare silanes represented by formula I.

The telogens containing two reactive halogen atoms, iodine or bromine, yield alpha, omega -telechelic telomers and cotelomers that can be linked to two different silicon atoms by means of non-halogenated alkylene radicals of 2, 3, 4 carbon atoms to obtain fluorinated polysilalkanes containing from 2 to 6 silicon atoms. To achieve the linear structure and the absence of significant crosslinking that characterizes the present organosilicon compounds, the synthesis must be properly organized with respect to the subsequent series of reactions of proper silanes with the telechelic dihalogeno telomers and with the monoiodo and/or monobromo telomers or cotelomers or with the other compounds described in this specification.

The telomerization process of the fluorinated vinyl compounds initiated by said telogens in accordance with the present invention can be promoted by heating or through activation by gamma-rays, ultra-violet irradiation, by organic peroxide initiators, redox systems containing copper or iron salts and amines or other reducing agents, metal carbonyls derived from elements in groups VI, VII and VIII of the Periodic Table, alkylated boron compounds and the addition of stoichiometric amounts of oxygen.

Preferred catalysts for these reactions include benzoyl peroxide, di-t-butyl peroxide, t-butylperoxypivalate and metal carbonyls where the metal is manganese, iron or chromium.

The reaction can be conducted in the presence of organic solvents including but not limited to 1,1,2-trichlorotrifluoroethane, t-butyl alcohol, acetonitrile, and mixtures thereof. Catalysts such as persulfate red-ox systems can also be included and the telomerization carried out in aqueous dispersion.

The temperature of telomerization ranges from ambient to 140° C., if the process is activated by irradiation, by catalysts, or within the range of 140° to 220° C. if the process is thermally activated.

The pressure under which the reaction is conducted can range from ambient up to about 60 atmospheres, and care should be taken to exclude oxygen from the telomerization reaction.

The fluorotelomers and -cotelomers are subsequently linked to the silicon atom of the present compounds through a halogen-free alkylene radical with 2,3,4 carbon atoms such as the dimethylene or trimethylene or tetramethylene radical, by a properly directed end-capping process. Ethylene is the reactant that can be easily used in the end-capping reaction.

As disclosed hereinbefore, when the telomer or cotelomer of non-hydrogenated vinyl compounds contains units derived from $C_2ClF_3$, and the highest thermostability is desired, to avoid possible dehalogenation or dehydrohalogenation, the telomerization process and the endcapping process must be conducted in order to minimize or forbid sequences =ClC—CCl=and to forbid the sequence=ClC—CH=.

When $C_2ClF_3$ is the only monomer, the telomerization should be conducted at temperatures not exceeding 100° C. Otherwise it is preferable to introduce a sufficient amount of another fluoroolefin for incorporation into the cotelomer to avoid as much as possible a "head-to-head" configuration due to sequences of $C_2ClF_3$ units.

In any instance, telomers or cotelomers of chlorotrifluoroethylene with other hydrogenated vinyl compounds, having one or two reactive terminal groups such as —CFClBr or —CFClI must be reacted in a final step, following removal of unreacted chlorotrifluoroethylene from the reaction vessel, with a perfluoroolefin such as $C_3F_6$ or $C_2F_4$ in a process referred to herein as pre-end capping. The final products are then end capped with a hydrogenated radical that can be made with ethylene.

When properly bonded to silicon as described hereinafter, telomerized fluoroolefins allow one to obtain high levels of chemical and thermal resistance and of lubricity for the final fluorinated organosilicon compound. Particularly, chains combining CTFE impart the property of low moisture absorption. The pre-endcapping step is not accomplished when the binary or ternary comonomer system contains chlorotrifluoroethylene and a hydrogenated olefin such as vinylidene fluoride.

Oligomers of Cyclic Fluoroethers (Oxetanes and Oxiranes)

The fluorinated oligomeric polyoxaalkylene intermediate compounds of this invention can be prepared using well known methods for the oligomerization of perfluorooxirane or fluorooxetanes such as perfluoropropenoxide, 2,2,3,3-tetrafluorooxetane, and 3,3,3-trifluoropropene oxide. Some of these oligomers are commercially available.

In accordance with a preferred method, the fluorinated polyoxaalkylene oligomers are prepared by reacting cesium fluoride or potassium fluoride with perfluorinated carbonyl compounds such as hexafluoroacetone, trifluoroacetyl fluoride, perfluoropropionyl fluoride, carbonyl fluoride, perfluorosuccinyl- or 1,5-oxaperfluoroglutaryl fluorides that are able to initiate the oligomerization of perfluorooxiranes and fluorooxetanes in accordance with known processes.

The resultant perfluorinated polyoxyalkylene carbonyl fluoride, must be reacted to form suitable intermediates able to be linked to silicon. A preferred method employs stoichiometric addition of potassium fluoride and subsequent substitution with allyl bromide to obtain allyl end-capped fluorinated polyoxyalkylene oligomers that are subsequently reacted with a reactive organohydrogensilane.

An alternative route for linking the present fluorinated poloxaalkylene oligomers to silicon is the metathesis of the terminal acid carbonyl fluoride groups of these oligomers to methyl esters and subsequent reduction to methanol radicals, followed by end-capping with allyl bromide using the known Williamson synthesis.

Reaction of the Fluorinated Telomers and Fluorinated Oligoners to Form Reactive Fluorinated Organosilicon Compounds Fluorinated telomers and oligomers terminated with one or two $(XC_1H_{21})$- groups, where X is bromine or iodine, can be converted to an organometallic derivative such as a Grignard reactant, Grignard-copper reactant, an organolithium, organozinc or organoaluminum compound, and subsequently reacted with a silane containing at least one halogen, such as chlorine or bromine, or at least one alkoxide group. The organometallic compound can be either preformed or formed in the presence of the silane.

Alternatively, the terminal alpha-iodo or alpha-bromo group of the polymethylene-terminated telomeric fluoroalkane, or the analogous telethelic alpha, omega-diiodo or -dibromo or -bromoiodo-polymethylenepolyfluoroalkane can be dehydrohalogenated to obtain, respectively, one or two terminal vinyl groups that can be reacted by a hydrosilation reaction with silanes containing at least one silicon-bonded hydrogen atom. This reaction is catalyzed by organic peroxides or platinum-containing catalysts.

In the case of silanes of formula I, in addition to the two atoms or groups required to react with the aforementioned derivatives of fluorinated telomers and oligomers of other groups, the silanes, after the reaction with monofunctional telomers and oligomers or with other groups, contain two reactive entities "X" as in formula I that can be subsequently reacted with other silanes to form the polysiloxane chain or, when trifunctional silanes are co-reacted, to form a crosslinked network. These two reactive entities include but are not limited to halogens such as chlorine and bromine, alkoxy groups containing from 1 to 4 or more carbon atoms, hydroxyl, and primary or secondary amino groups.

The crosslined network can be accomplished in the following step after the polycondensation to polysiloxane, through reaction of some alkenyl groups. In the case of formula II, the silanes that are reacted with difunctional derivatives of telomers or oligomers, or other groups, and with monofunctional derivatives of telomers or oligomers or other groups, require one of the aforementioned reactive entities X at each of the two telechelic silicon atoms present at the end of the molecule represented by the formula II. Said reactive entities X are subsequently reacted with other silanes to form a chain-extended or crosslinked structure as said before.

As for intended applications, which should not be considered as limitative of the invention, where the final fluorosilicone must exist as a liquid or wax over a wide range of temperatures, there are critical structural parameters required for this purpose that include, besides the proper molecular weight range, a random distribution of repeating units in the telomeric chains and random distribution of the different fluoroalkyl groups linked to the same silicon atom. These paremeters can be achieved by reaction of the silicon-containing reactant with the different groups according to the invention in subsequent steps, and in the case of the synthesis of diakylsilanes corresponding to formula I, also in simultaneous co-reactions. The silanes of formula I and/or II are polycondensated in order to build polysiloxane chains where the units I and/or II are linked in homo- or copolymers, in random or ordered sequences.

The units with the structures represented by formulae I and II can be properly homopolycondensated separately to form homogeneus block type I and block type II, or copolycondensated in random sequences of units I and II by the usual procedures of silicone chemical technology well known to those skilled in the art. When necessary, in the case of elastomeric materials, the structure of the chain must contain proper crosslinkable units. Particularly when the chains contain units carrying vinyl groups, the crosslinks can be achieved by platinum catalized silanization reactions and using polyhydrosilanes as crosslinkers.

An alternative mechanism of crosslinking can be achieved by inserting in the main chain some silane units carrying branches such as $-C_2H_4C_2F_4Br$ that can be involved in the crosslinking mechanism by the action of peroxide, type VAROX, and triallylisocyanurate.

It will be understood that when preparing organosilicon compounds containing two or more silicon atoms per molecule the sequence of said reactions is adjusted to achieve the desired number of silicon atoms in the final polysilalkane chain, which can contain from two to six silicon atoms.

In summary, the preferred reactions for preparing the present fluorosilicone compounds from fluorotelomers or cotelomers, from fluoropolyether oligomers or from other groups according to the invention, include:

$$R_fX + M' + M'' \longrightarrow R_f(M')_p(M'')_qX \quad (A) \quad (1)$$

M', M'' = fluoroolefins and/or perfluoroalkyl vinyl ethers

If M' = $C_2ClF_3$, A + $RCF=CF_2 \longrightarrow$ (2)

$$R_f(M')_p(M'')_qCF_2-CFRX \quad (B)$$

R = F or $CF_3$ (pre end capping step)

B + $C_2H_4 \longrightarrow$ (3)

$$R_f(M')_p(M'')_qCF_2-CFRC_2H_4X \quad (C) \text{ (end capping step)}$$

C + Me $\xrightarrow{-X_2SiY}$ (4a)

$$R_f(M')_p(M'')_qCF_2-CFRC_2H_4SiX_2-$$

Me = metal Mg, Li, Mg/Cu, Zn, Al; Y = Br, Cl, alkoxy

C + KOH $\xrightarrow{-X_2SiH}{\text{(Pt catalyst)}}$ (4b)

$$R_f(M')_p(M'')_qCF_2-CFRC_2H_4SiX_2-$$

Pt = Pt/C, $H_2PtCl_6 \cdot 6H_2O$ $$R'-CO-R'' \xrightarrow{CsF} R'(R'')CFOCs \quad (D) \quad (5)$$

R' and R'' are F and/or $CF_3$; moreover when R' = F, R'' is $-CF_3, -C_2F_5, -COF, -C_2F_4COF, -CF_2OCF_2COF$ D + $nR^1\overline{CFCF_2-O} \longrightarrow$ (6)

$$R'R''CFO(R^1CFCF_2O)_nCFR'COF \quad (E) + F^-Cs^+$$

where $R^1$ is fluorine or trifloromethyl

D + $\overline{CH_2CF_2CF_2O} \longrightarrow$ (7)

$$R'R''CFO(C_3H_2F_4O)_nCH_2CF_2COF \quad (G) + F^-Cs^+$$

R*COF $\xrightarrow{KF} \xrightarrow{BrCH_2CH=CH_2}$ (8)

$$R^*CF_2OCH_2-CH=CH_2 + KBr$$

R*COF = E or G

R*COF $\xrightarrow{H_2}{\text{or } H^-}$ (9)

$$R^*CH_2OH \xrightarrow{BrCH_2CH=CH_2} R^*CH_2OCH_2-CH=CH_2$$

The products of reactions 8 or 9 can be reacted with an organohydrogensilane as shown in reaction 4b.

The fluoroalkyl aromatic building block $R^3$ (in the repeating unit of the formula II) can have the structure:

$$-(OC(CF_3)_2-C_6H_4C(CF_3)_2OC_6H_4SO_2C_6H_4-)_m-O-C(CF_3)_2C_6H_4C(CF_3)_2-O- \quad 10)$$

that is linked to silicon atoms through allyl ether bridges as from reaction 9.

Particularly preferred fluorinated organosilicon compounds of this invention exhibit one of the following structures:

a) $(R''fC_1H_{21})_2SiX_2$, where R''f represent the same or preferably different polyfluoroalkylene or polyfluoropolyoxaalkylene groups that are preferably obtained using the procedures and reactions described hereinabove, X represents one of reactive entities described hereinbefore, "1" is 2 or 3 for polyfluoroalkylene telomers or 3 for polyfluoropolyoxaalkylene oligomers; or

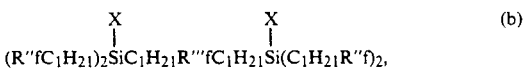

(b)

where R''f and "1" are defined above in (a), R'''f is a divalent alpha,omega fluoroalkylene or alpha,omega-poly-oxafluoroalkylene radical, or a arylenoxy radical such as bisphenol AF or an oxyfluoroalkyl substituted arylene radical such as 1,3-bis(hexafluoro-2-isopropyl)-benzene.

Due to the random sequences of selected and proper units within the groups $R^1$, $R^2$, $R^3$ linked to silicon, random substitution of these groups to the larger radius of the silicon atom, absence of halogenated carbon atoms located in the alpha or beta positions with respect to the silicon, presence of flexible ether segments and highly fluorinated carbon segments, the polyorganosiloxanes prepared using the present fluorinated organosilicon compounds exhibit, among other properties reported hereinafter, low values of surface energy (30 to 20 dynes/cm), that is reflected in their low friction coefficient and high lubricity, hydro-oleophobicity that moreover protect the bonds between silicon and carbon or oxygen from chemical attack of aggressive chemicals when carried in solubilized form.

Depending upon the nature of the reactive entities "X" on the silicon atom(s) of these organosilicon compounds, possible presence of known silanes carrying one or three reactive entities X, said silanes of formula I and/or II are polymerized in the desired molecular weight linear silicone or crosslinked elastomers and resins under ambient conditions in the presence of moisture and a suitable catalyst, or by blending the linear polysiloxane containing reactive sites with an organic peroxide and heating the resultant mixture to a temperature above the decomposition temperature of the peroxide, or by blending the compounds of the invention with a suitable curing agent containing at least two reactive groups that will react with the reactive sites present in said compound. Such curing agents and catalysts are sufficiently well known that a detailed description is not required in this specification.

The properties of the final polymers obtained according to the invention and depending on their structure include, but are not limited to:

low dielectric constant and high resistivity and dielectric strength
good optical properties due to low refractive index
high resistance to solvents and aggressive chemicals
high resistance to oxygen also at high temperature
high resistance to depolymerization
non-flammability
good rheological properties (for rubbers and liquids)
resistance to irradiation and to high energy particles
high mechanical resistance (for rubbers and resins)

These properties allow the use of the crosslinked fluoroalkylsilanes, one species obtained from the present fluorinated organosilicon compounds, as high performance barrier and release materials containing optical, electrical insulating and weather resistance properties, sealants resistant to oils and other chemicals, high consistency rubbers that can be profitably reinforced with special carbon black to obtain high mechanical resistance and also resistance to fatigue and abrasion, and resins with good anti-wear properties.

The aforementioned properties allow the use of linear fluorosilicones, another part of the invention, as hydraulic fluids and lubricants, ingredients for greases, electrical insulating fluids and optical media.

Without further elaboration it is believed that one skilled in the art, using the preceding decription, can utilize the present invention to its fullest extent. The following examples are, therefore, to be construed as merely illustrative, and not limitative in any way whatsoever, of the remainder of the disclosure or claims. The examples, while they have not actually been carried out, describe preparative methods that are expected to yield preferred embodiments of the present invention. Unless otherwise specified all parts and percentages specified in the examples are by weight and viscosities are based on a temperature of 25° C.

EXAMPLE I

Reactive Fluorinated Silanes and Their Polymers From Telomers of Chlorotrifluoroethylene Step 1

A stainless steel autoclave of 2 l. capacity is charged under an inert atmosphere with t.butylperoxy-pivalate (15 g), CF₃I (1570 g, from PCR, Inc.) and CTFE (466 g). The reaction is started at 80° C. and continued for 5 hours, then the temperature is increased to 100° C. in 8 hours.

The reactor is cooled, any unreacted gasses are continuously discharged and the liquid residue is distilled through a Todd column at reflux ratio of 20 to obtain products corresponding to the general structure:

$$CF_3-(CF_2CFCl)_nI \qquad IA$$

| Product | Title |
|---------|-------|
| n = 1   | 95%   |
| n = 2   | 95%   |
| n = 3   | 95%   |
| n-4-7   | (residue) |

These products can be identified and recognized by infrared and liquid-gas chromotography.

While telogens and telomers, wherein n=1, are recycled, telomers wherein n has a value of 2 or 3 (IA) are collected between 70° and 120° C. at a pressure of 30 mm Hg and are used in subsequent steps.

Step 2

A stainless steel autoclave of 250 ml. capacity is charged with 140 g of telomers $CF_3(C_2F_3Cl)_nI$, where n=2 and 3 (prepared as described in Step 1), and 100 g of HFP. The reaction is initiated by heating at 150°-200° C. for 24 hours. The reaction then is allowed to cool overnight, any unreacted gas is discharged, and a liquid product is obtained. This liquid is distilled in a Todd column at 5 mm Hg collecting, at reflux ratio of 10, a major fraction in the range of from 80° to 110° C. Analysis of this fraction by infrared and gas-liquid chromotography is expected to be consistent with the starting product and with the structure $$CF_3(C_2F_3Cl)_nC_3F_6I \qquad IB$$

where n=2,3.

Step 3

A glass lined autoclave of 500 ml is charged with 0.1 g CuCl, 3 g ethanolamine, 200 ml t-butyl alcohol and 100 g of product IB. The autoclave is then connected through a steel pipe to a cylinder of ethylene that is allowed to enter at 30 atm. The reactor is then heated at 100° C. for 16 hours with shaking. The reactor is cooled, any unreacted gas is discharged, the contents of the reactor is poured in cool aqueous 25% H Cl, is washed with cold water and is dried on magnesium sulfate. The infrared analysis is expected to be indicative of the structure:

$$CF_3(C_2F_3Cl)_nC_3F_6-C_2H_4I \qquad IC$$

where n=2, 3.

This product IC is dehydrohalogenated at 100° C. over KOH in ethanol according to the procedure described in the "Journal of Org. Chem" 36, (18) 2596 1971 by D. J Burton, to obtain $$CF_3(C_2ClF_3)_nC_3F_6CH=CH_2 \qquad ID$$

where n=2, 3, as could be verified by infrared and L.G.C. analysis.

Step 4

The silanization of Product ID is carried out according to the procedure reported by J. L. Speier, "Adv. Organomet. Chem.", vol. 17, page 407, (1979), with methyl dichlorosilane in the presence of catalyst H₂PtCl₆.6H₂O to obtain the product:

$$CH_3SiCl_2[C_2H_4C_3F_6(C_2ClF_3)_n-CF_3] \qquad IE$$

The identity of this product can be determined using elemental and NMR analysis, while L.G.C. should confirm the distribution of components where n=2,3.

Step 5

Product IE (50g) and 0.1 g of dimethylvinylchlorosilane are reacted with stoichiometric water in the presence of 0.2 g of guanidine chlorohydrate, while nitrogen is bubbled in. The temperature is increased progressively to 80° C. in 8 hours and a polysiloxane gum is separated that is dried under vacuum at 80° C. to produce a product IF, which should exhibit a glass transition temperature using differential scanning calorimetry of lower than −40° C.

A sample of 20g of the gum is passed under a laboratory scale 3-roll mill and charged with 6 g of fumed silica, 02 g of VAROX and 0.4 g triallylcyanurate. The slab is put inside a molding mask under Carver press plates for 30 minutes at a temperature of 130° C., followed by 7 hours at a temperature of 170° C. A flat slab 1 mm thick is expected to show good mechanical properties with a tensile strength at break and elongation typical for cured silicone elastomers.

EXAMPLE 2

Reactive Fluorinated Silanes and Their Polymers from Telechelic Cotelomers of CTFE Step 1

The same procedure of Example 1 is followed, with the exception that a 2 liter capacity autoclave is charged with 15 g of t-butylperoxypivalate and 710 g of IC₂F₄I (obtained from PCR, Inc.). CTFE 440 g and 360 g of hexafluoropropene are introduced into the autoclave.

The reaction is started by heating at 80° C. for 26 hours, while the temperature is progressively increased to 130° C. After overnight cooling, any unreacted gasses are discharged. The liquid remaining is distilled within the range between 100° and 250° C. under a pressure of 1 mm Hg to yield a product that by infrared and gas liquid chromatography analysis will be found to contain random cotelomers according to the formula:

$$I(C_2F_3Cl)_p(C_2F_4)(C_3F_6)_qI \qquad \text{IIA}$$

where the average ratio p/q is equal to 3 and p+q is in the range of from 3-5.

Steps 2 and 3

By the same procedures described in Example 1, 100 g of product IIA is reacted with hexafluoropropene, then ethylene, and then finally dehydrohalogenated to the product:

$$CH_2=CH-C_3F_6(C_2ClF_3)_p(C_2F_4)(C_3F_6)_qC_3F_6-CH=CH_2 \qquad \text{IIB}$$

Step 4

In a liter pyrex flask fitted with a stirrer and dropping funnel and kept in a nitrogen atmosphere, there is charged 0.1 g of 1% pt/g, 105 g of product IIB and methyldiethoxysilane (32 g). The mixture is stirred while the flask is heated to 80° C. and bubbled with dry nitrogen to let excess silane evaporate. Then the mixture is filtered and is transferred to a new 2 l flask, also fitted with a dropping funnel and stirrer, then diluted with 500 ml ethylether to obtain a solution of reactive telechelic organic disilane with the expected structure:

$$(C_2H_5O)_2CH_3SiC_2H_4C_3F_6(C_2ClF_3)_p(C_2F_4)(C_3F_6)_qC_3F_6C_2H_4SiCH_3(OC_2H_5)_2 \qquad \text{IIC}$$

Step 5

A Grignard reagent prepared from 1-iodo-3,3,3 trifluoropropane (53 g) and 7.5 g of Mg in 500 ml of ethylether is added to the product IIC at a rate sufficient to maintain the reaction mixture at reflux for 10 hours. After overnight cooling, the mixture is poured in a stirred mixture of ice and ammonium chloride solution. The organic layer is washed with cold water and the solvent evaporated at 40° C. under vacuum. A viscous liquid residue is obtained whose elemental and NMR analyses are expected to be consistent with the starting product and with the structure:

$$AO[SiR^3R^4C_2H_4C_3F_6(C_2ClF_3)_p(C_2F_4)-(C_3F_6)_qC_3F_6C_2H_4SiR^3R^4O]_nA \qquad \text{IID}$$

where $R^3 = C_2H_4CF_3$, $R^4 = CH_3$ and A=H or $C_2H_5$.

The product IID corresponds to a mixture of components with n from 1 to 4, that can be identified according to the viscosity of the fluids and by gel chromatography.

Step 6: Compounding and Crosslinking

The product IID (50 g) is mixed with 01 g of dimethyl vinyl chlorosilane and 10 ml of toluene, and 0.2 g of tetramethylguanidine acetate is stirred at reflux temperature, then heated at a temperature from 30° to 100° C. for 6 hours while nitrogen is bubbled in. A consistent gum is expected according to this procedure.

When 20 g of this gum is compounded as described in step 5 of Example I (but compounded with carbon medium thermal) and crosslinked at temperatures from 130° to 170° C., it is predicted that a very mechanically resistant rubber slab results which is expected to show a tensile strength at break higher than the sample of Example 1.

EXAMPLE 3

Reactive Fluorinated Silanes and Their Polymers from Telechelic Cotelomers of Fluoroolefins A cotelomer product can be prepared according to the procedure of Example 2, but starting from 175 g vinylidene fluoride (VDF), 90 g tetrafluoroethylene (TFE), and 360 g HFP. As predictable from the well known reactivity ratios of the monomers, the final product has the structure:

$$I(VDF)_m(TFE)_n(HFP)_p I \qquad \text{IIIA}$$

where the IR spectroscopy is expected to confirm the ratio m:n:p corresponding to 3:1:1.

The product is then reacted with ethylene and dehydrohalogenated to the telechelic divinyl:

$$C_2H_3(VDF)_m(TFE)_n(HFP)_pC_2H_3 \qquad \text{IIIB}$$

whose structure can be verified by 19F-NMR analysis. See, e.g., Polymer, Vol. 28, page 224, 1987.

The same procedures as in steps 4, 5 of Example 2 can be applied to obtain a telechelic disilane compound with the expected structure:

$$AO[SiR^3R^4C_2H_4(VDF)_m(TFE)_n(HFP)_pC_2H_4SiR^3R^4O]_nA \qquad \text{IIIC}$$

where $R^3=C_2H_4CF_3$, $R^4=CH_3$, A=H or $C_2H_5$, and whose identity can be verified by NMR analysis.

Then the product is reacted as in step 6 of Example 2 with dimethyl vinylchlorosilane. The final gum product is passed in a 3 roll mill and mixed with polyhydrosiloxane (02 parts) and $10^{-5}$ parts phr of inhibited chloroplatinic acid and the formulation is passed several times on the roll mill to obtain a final slab of homogeneous rubber.

Then the slab is put under a Carver press at 80° C. for 5 minutes. After cooling there should be obtained a thin crosslinked foil which is transparent and exhibits excellent mechanical resistance. Samples of crosslinked elastomer, after immersion in different solvents at 23° for 170 hours are expected to show swelling volume change within the limit of 5% in heptane and 3%-5% in ethanol.

EXAMPLE 4

Preparation of Organosilicon Compound Having Two Silicon Atoms Per Molecule

Bis-(2-hydroxyhexafluoro-propene) benzene (A), that can be obtained from excess hexafluoroacetone with benzene as described in U.S. Pat. No. 2,443,003, and "Journal of American Chemical Society", 87, 2410 (1965), is reacted with ClC₆H₄(C₂F₄)₂C₆H₄—Cl (B) obtained according to the "Brit. Polymer Journal", (1970), 288, in ratio of A:B of 2:1 at 100° C. under nitrogen stream to vent HCl. The final dialcohol (C), as the sodium salt, is reacted with allyl bromide and converted to diallylether and then with excess 3,3,3-trifluoropropylmethylchlorosilane, in the presence of Pt catalyst to form a bis chlorosilane according to the structure:

$$ClSiR^3R^4-[C_3H_6OC(CF_3)_2C_6H_4C(CF_3)_2-OC_6H_4\\-C_4H_{10}C_6H_4OC(CF_3)_2\\C_6H_4(CF_3)_2COC_3H_6]SiR^3R^4Cl \quad \text{IV}$$

where $R^3=CH_3$, $R^4=C_2H_4CF_3$.

The product IV is reacted with stoichiometric water as described in Example 1, step 5, and a resin is obtained that is moldable to a transparent film under press plates at 250° C. The film is expected to show a contact angle higher than 110° C. versus drops of water.

The preceding Examples can be repeated with similar success by substituting the other generically or specifically described reactants and/or operating conditions of this invention for those used in the preceding Examples.

The foregoing is considered illustrative only of the principles of the invention. Further, since numerous modifications and changes will readily occur to those skilled in the art, it is not desired to limit the invention to the exact reagents, amounts, steps, etc., shown and described. Accordingly, all suitable modifications and equivalents may be resorted to that fall within the scope of the invention and the appended claims.

That which is claimed is:

1. A fluorinated organosilicon compound corresponding to the formula $$X_2R^1{}_2Si \quad \text{I}$$

or $$XR^2{}_2Si(R^3SiR^2{}_2)_zX \quad \text{II}$$

wherein X is a reactive group selective from chlorine, hydroxyl, alkoxy, acetoxy, amino, alkyl amino and dialkyl amino, z is from 1 to 5 inclusive, at least one of the $R^1$ radicals of formula I and at least one of the $R_2$ radicals bonded to each of the silicon atoms of formula II are selected from the group consisting of
1) telomers and cotelomers represented by the formulae
$Rf(C_2F_4)_t(C_2H_2F_2)_u(C_2ClF_3)_qC_1H_{21}-$,
$Rf(C_2H_2F_2)_p(C_3F_6)_qC_1H_{21}-$,
$Rf(C_2H_2F_2)_t(C_2ClF_3)_u(C_3F_6)_qC_1H_{21}-$,
$Rf(C_2ClF_3)_nCF_2CF(R^4)C_1H_{21}-$,
$Rf(C_2ClF_3)_p(C_3F_6)_qC_3F_6C_1H_{21}-$,
$Rf(C_2F_4)_t(C_2ClF_3)_u(C_3F_6)_qCF_2CF(R^4)C_1H_{21}-$,
$Rf(C_2F_4)_t(C_2ClF_3)_u[C_2F_3(ORf)]_qC_2F_4C_1H_{21}-$
$Rf(C_2H_2F_2)_p(C_3F_6)_qC_1H_{21}-$,
$Rf(C_2ClF_3)_p[C_2F_3(ORf)]_qCF_2CF(R_4)C_1H_{21}-$,
wherein the repeating units of said cotelomers are randomly distributed within the molecules, and
2) oligomers corresponding to the formula
$R'fO(C_3F_6O)_mCF(CF_3)CA_2OC_3H_6-$,
$C_3F_7O(C_3H_2F_4O)_m-CH_2CF_2CA_2OC_3H_6-$, or
$R^5O(CF_3C_2H_3O)_mC_3H_6-$, where A is hydrogen or fluorine,
$R^4$ is fluorine or a trifluoromethyl group,
$R^5$ is an alkyl or fluoroalkyl radical,
Rf is $-CF_3$, $-C_2F_5$, $-C_3F_7$ or $-C_4F_9$,
R'f is $-CF_3$, $C_2F_5$ or $C_3F_7$;
the value of l is 2, 3, or 4,
where any $R^1$ and $R^2$ radicals that do not represent said telomer, cotelomer or oligomer is methyl, 3,3,3-trifluoropropyl, phenyl or perfluoroalkyl substituted phenyl, said perfluoroalkyl group containing from 1 to 3 carbon atoms;
where $R^3$ is selected from
$-C_1H_{21}-C_3F_6(C_2ClF_3)_n(T)C_3F_6-C_1H_{21}-$,
$-C_1H_{21}-C_2F_4(C_2ClF_3)_u(T)(C_2F_4)_t(C_2F_3ORf)_q-C_2F_4-C_1H_{21}-$,
$-C_1H_{21}-C_3F_6(C_2ClF_3)_u(T)(C_2F_4)_t(C_3F_6)_q-C_3F_6-C_1H_{21}-$.
$-C_1H_{21}C_3F_6(C_2ClF_3)_p(T)(C_3F_6)_q-C_3F_6C_1H_{21}-$,
$-C_1H_{21}(C_2H_2F_2)_p(T)(C_3F_6)_q-C_1H_{21}-$,
$-C_1H_{21}(C_2F_4)_p(T)(C_2F_3ORf)_qC_1H_{21}-$,
$-C_1H_{21}(C_2H_2F_2)_p(T)(C_2ClF_3)_q-C_1H_{21}-$,
$-C_1H_{21}(C_2H_2F_2)_t(C_2F_4)_u(T)(C_3F_6)_q-C_1H_{21}-$,
$-C_3H_6O(CF_3)_2C-C_6H_4-C(CF_3)_2OC_3H_6-$,
$-C_3H_6OCA_2CF_2CH_2O(C_3H_2F_4O)_gT'O(C_3H_2F_4O)_g-CH_2CF_2CA_2OC_3H_6-$,
$-C_3H_6OCH_2CF_2O(C_2F_4O)_h(CF_2O)_iCF_2CH_2OC_3H_6-$, and
$-C_3H_6OCA_2-CF(CF_3)O(C_3F_6O)_gT'O(C_3F_6O)_gCF(CF_3)CA_2OC_3H_6-$, where T is selected from the group consisting of $-C_2F_4-$, $-C_3F_6-$, $-C_2ClF_3-$, $-C_4F_8-$, $-C_6F_xH_{(4-x)}-$ and $O[C_6F_xH_{(4-x)}]_2$; and x is from 2 to 4, inclusive,
T' is selected from $-C_2F_4-$, $-C_4F_8-$, $-C_5F_{10}-$ or $-(C_2F_4)_2O-$,
the value of n is from 1 to 20, inclusive, the value of p/g is from 2 to 10, inclusive, the value of p+g is from 2 to 20, the value of t+u/g is from 2 to 10, inclusive, the value of t/u is from 0.1 to 10, the value of t+u+g is from 2 to 20, inclusive, the value of m is from 1 to 20, inclusive, the value of g is from 1 to 20, inclusive, the value of h/i is from 0.5 to 20, inclusive and the value of h+i is from 8 to 100, inclusive.

2. The compound as recited in claim 1, wherein at least one of the non terminal $R^2$ radicals is said monovalent telomer, cotelomer or oligomer.

3. The compound according to claim 1, wherein the fluorinated olefin of the monovalent telomer is chlorotrifluoroethylene, vinylidene fluoride or trifluoroethylene.

4. The compound according to claim 1, wherein the fluoropropene is hexafluoropropene, 1-H-pentafluoropropene or 2-H-pentafluoropropene.

5. The compound according to claim 1, wherein the fluoroethylene is tetrafluoroethylene or trfluoroethylene.

6. The compound according to claim 1, wherein the oligomerization of the fluorinated oxiranes and oxetanes is initiated using as a reaction product a perfluorinated carbonyl compound with cesium fluorine or potassium fluoride.

7. The compound according to claim 1, wherein the telomerization or cotelomerization is initiated by using as reactant a monoiodo or monobromo telogen.

8. The compound according to claim 1, wherein the telomerization or cotelomerization is initiated by using as a reactant a diiodo or dibromo, iodobromo telogen.

9. The compound according to claim 6, wherein said perfluorinated carbonyl compound is a hexafluoroacetone, trifluoroacetyl fluoride, perfluoropropionylfluoride, perfluorsuccinyl fluoride or 1,5-oxyfluoroglutary fluoride.

10. A compound according to claim 1 where X represents chlorine and $R^1$ represents $Rf(C_2ClF_3)_n-CF_2CF(R^4)CH_2CH_2-$, where $Rf$ represents $C_2F_5$, $R^4$ represents trifluoromethyl and the value of n is from 1 to 4 with an average value of 2.

* * * * *